(12) United States Patent
Gemborys

(10) Patent No.: US 10,029,033 B2
(45) Date of Patent: *Jul. 24, 2018

(54) ENCAPSULATED DRUG COMPOSITIONS AND METHODS OF USE THEREOF

(71) Applicant: COOK MEDICAL TECHNOLOGIES LLC, Bloomington, IN (US)

(72) Inventor: Colleen Gemborys, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/496,466

(22) Filed: Apr. 25, 2017

(65) Prior Publication Data

US 2017/0224878 A1 Aug. 10, 2017

Related U.S. Application Data

(63) Continuation of application No. 14/454,345, filed on Aug. 7, 2014, now Pat. No. 9,655,998.

(51) Int. Cl.
| | |
|---|---|
| *A61L 29/16* | (2006.01) |
| *A61L 31/16* | (2006.01) |
| *A61L 31/10* | (2006.01) |
| *A61L 29/08* | (2006.01) |

(52) U.S. Cl.
CPC ............. *A61L 29/16* (2013.01); *A61L 29/085* (2013.01); *A61L 31/10* (2013.01); *A61L 31/16* (2013.01); *A61L 2300/416* (2013.01)

(58) Field of Classification Search
None
See application file for complete search history.

(56) References Cited

U.S. PATENT DOCUMENTS

| | | |
|---|---|---|
| 8,192,479 B2 | 6/2012 | Paul |
| 8,642,063 B2 | 2/2014 | Sarasam et al. |
| 8,916,227 B2 | 12/2014 | Horres et al. |
| 9,180,226 B1 | 11/2015 | Jackson et al. |
| 9,572,914 B2 | 2/2017 | Jackson et al. |
| 9,655,998 B2 | 5/2017 | Gemborys |
| 2003/0044474 A1 | 3/2003 | Tao et al. |
| 2005/0019404 A1 | 1/2005 | Sung et al. |
| 2005/0027000 A1 | 2/2005 | Reed et al. |
| 2005/0037048 A1 | 2/2005 | Song |
| 2005/0064011 A1 | 3/2005 | Song et al. |
| 2005/0119404 A1 | 6/2005 | Luo et al. |
| 2005/0163821 A1 | 7/2005 | Sung et al. |
| 2006/0034885 A1 | 2/2006 | Sung et al. |
| 2006/0040894 A1 | 2/2006 | Hunter et al. |
| 2007/0054868 A1 | 3/2007 | Weinstein |
| 2007/0141100 A1 | 6/2007 | Sung et al. |
| 2007/0178138 A1 | 8/2007 | Pal et al. |
| 2008/0020013 A1* | 1/2008 | Reyes .................... A61F 2/91 424/423 |
| 2008/0103103 A1 | 5/2008 | Memarzadeh et al. |
| 2008/0255510 A1 | 10/2008 | Wang |
| 2010/0168837 A1 | 7/2010 | Magnuson et al. |
| 2010/0233228 A1 | 9/2010 | Speck |
| 2010/0261662 A1 | 10/2010 | Schreck et al. |
| 2010/0272773 A1 | 10/2010 | Kangas et al. |
| 2010/0285085 A1 | 11/2010 | Stankus et al. |
| 2011/0008260 A1 | 1/2011 | Flanagan et al. |
| 2011/0015664 A1 | 1/2011 | Kangas et al. |
| 2011/0033525 A1 | 2/2011 | Liu |
| 2011/0111057 A1 | 5/2011 | Reed et al. |
| 2011/0144577 A1 | 6/2011 | Stankus et al. |
| 2011/0171128 A1 | 7/2011 | Beliveau et al. |
| 2011/0195910 A1 | 8/2011 | Ling et al. |
| 2012/0148567 A1 | 6/2012 | Kurisawa et al. |
| 2012/0156135 A1 | 6/2012 | Farokhzad et al. |
| 2012/0269901 A1 | 10/2012 | Reed et al. |
| 2012/0277719 A1 | 11/2012 | Shukla et al. |
| 2012/0277852 A1 | 11/2012 | Shukla et al. |

(Continued)

FOREIGN PATENT DOCUMENTS

| | | |
|---|---|---|
| EP | 2 098 230 B1 | 6/2012 |
| EP | 2 962 707 A1 | 1/2016 |

(Continued)

OTHER PUBLICATIONS

Wang, Huang-Joe et al., "(−)Epigallocatechin-3-gallate decreases thrombin/paclitaxel-induced endothelial tissue factor expression via the inhibition of c-Jun terminal NH2 kinase phosphorylation", *Biochemical and Biophysical Research Communications*, 2010, vol. 391, pp. 716-721.
Extended European Search Report for EPO15179160 dated Dec. 7, 2015, 7 pgs.
Extended European Search Report for EPO15179148 dated Dec. 7, 2015, 7 pgs.
Japanese Office Action with English language translation for related application No. JP 2015-153847 dated Aug. 16, 2016, 7 pages.
Japanese Office Action with English language translation for related application No. JP 2015-155874 dated Aug. 24, 2016, 5 pgs.
Examination Report for EP1519148.0 dated Oct. 26, 2016, 5 pgs.
Office Action, and English language translation thereof, in corresponding Japanese Application No. 2015-155874, dated Jul. 5, 2017, 5 pages.
Office Action for U.S. Appl. No. 15/386,662 dated Oct. 25, 2017, 10 pgs.
Response to Japanese Office Action in correpsonding Japanese Application No. 2015-155874, dated Dec. 1, 2017, 5 pages (English translation).
Decision for Patent and English language translation thereof, in corresponding Japanese Application No. 2015-155874, dated Dec. 20, 2017, 4 pages.
Response to Japanese Office Action, and English language translation thereof, in corresponding Japanese Application No. 2015-153847, dated Jan. 16, 2017, 5 pages.

(Continued)

*Primary Examiner* — Robert A Wax
*Assistant Examiner* — Quanglong Truong
(74) *Attorney, Agent, or Firm* — Brinks Gilson & Lione

(57) ABSTRACT

Various aspects of the present disclosure provide compositions, coatings and implantable devices including a drug and an excipient. In certain embodiments the excipient and the drug are present at a weight ratio of between 10 to 1 and 1 to 10 drug to excipient. In certain other embodiments, the excipient and the drug form particles in which the drug is encapsulated by the excipient. Other aspects of the disclosure provide methods of manufacturing and using such compositions, coatings and implantable devices.

19 Claims, 8 Drawing Sheets

(56) References Cited

U.S. PATENT DOCUMENTS

| | | |
|---|---|---|
| 2012/0316633 A1 | 12/2012 | Flanagan et al. |
| 2012/0323211 A1* | 12/2012 | Ogle .................. A61K 47/32 604/500 |
| 2012/0329738 A1 | 12/2012 | Liu |
| 2013/0004488 A1 | 1/2013 | Kurisawa et al. |
| 2013/0046237 A1* | 2/2013 | Speck .................. A61L 29/16 604/103.02 |
| 2014/0227192 A1 | 8/2014 | Speck et al. |
| 2014/0227193 A1 | 8/2014 | Speck et al. |
| 2014/0227194 A1 | 8/2014 | Speck et al. |
| 2017/0100524 A1 | 4/2017 | Jackson et al. |

FOREIGN PATENT DOCUMENTS

| | | |
|---|---|---|
| EP | 2 982 388 A1 | 2/2016 |
| EP | 2 982 389 A1 | 2/2016 |
| EP | 2 944 332 B1 | 8/2016 |
| EP | 2 709 711 B1 | 11/2016 |
| EP | 2 857 049 B1 | 11/2016 |
| JP | 2007-526793 A | 9/2007 |
| JP | 2008-253707 A | 10/2008 |
| JP | 2012-533338 A | 12/2012 |
| WO | WO 2000/32238 A1 | 6/2000 |
| WO | WO 2010/124098 A2 | 10/2010 |
| WO | WO 2011/019323 | 2/2011 |
| WO | WO 2011/071630 A1 | 6/2011 |
| WO | WO 2011/112156 A1 | 9/2011 |
| WO | WO 2013/053809 | 4/2013 |
| WO | WO 2013-053809 A1 | 4/2013 |
| WO | WO 2015/171079 A1 | 11/2015 |
| WO | WO 2017/072545 A1 | 5/2017 |

OTHER PUBLICATIONS

Decision for Patent and English language translation thereof, in corresponding Japanese Application No. 2015-153847, dated May 2, 2017, 6 pages.

Response to Search Opinion in corresponding European Application No. 15179160.5, dated Aug. 9, 2016, 10 pages.

Response to Search Opinion in corresponding European Application No. 15179148.0, dated Aug. 10, 2016, 11 pages.

Response to Office Action in corresponding European Application No. 15179148.0, dated Mar. 31, 2017, 62 pages.

Intention to Grant in corresponding European Application No. 15179148.0, dated Oct. 23, 2017, 71 pages.

Office Action for Japanese Application No. 2017-11242, dated Feb. 13, 2018, 7 pgs.

* cited by examiner

ENCAPSULATED DRUG COMPOSITIONS AND METHODS OF USE THEREOF

RELATED APPLICATIONS

This patent application is a continuation of U.S. patent application Ser. No. 14/454,345, filed Aug. 7, 2014, the entire contents of which application is hereby incorporated by reference.

TECHNICAL FIELD

The present disclosure generally relates to compositions including a drug encapsulated by an excipient, to devices including such compositions and to methods of preparing and using such compositions and devices.

BACKGROUND

Local delivery of a therapeutic agent can be useful in the treatment of many medical conditions. Illustratively, local delivery of a therapeutic agent within a body vessel or to a selected portion of internal body tissue can eliminate or reduce the need for systemic delivery of the therapeutic agent thus minimizing any potential adverse effect of the therapeutic agent on areas of the body not needing treatment.

Minimally invasive implantable medical devices, such as balloons, catheters and stents, can provide a platform for delivering therapeutic agents to internal body tissue. For example, balloon catheters or stents may be used to deliver a therapeutic agent directly to the target site within a body vessel such as an artery or vein.

One example of a condition that can be beneficially treated by local administration of a therapeutic agent with a balloon catheter is the delivery of a therapeutic agent in combination with percutaneous transluminal coronary angioplasty (PTCA), a technique used to dilate stenotic portions of blood vessels. Although PTCA and related procedures aid in alleviating intraluminal constrictions, such constrictions or blockages may reoccur in many cases. The cause of these recurring obstructions, termed restenosis, may be due to the body responding to the surgical procedure. Restenosis of the vessel may develop over several months after the procedure, and may require another angioplasty procedure or a surgical bypass operation to correct. Proliferation and migration of smooth muscle cells (SMC) from the media layer of the lumen to the intimal layer cause an excessive production of extracellular matrices (ECM), which is believed to be one of the leading contributors to the development of restenosis. The extensive thickening of tissues narrows the lumen of the blood vessel, constricting or blocking the blood flow through the vessel.

Drugs that inhibit restenosis may be locally delivered during PTCA from a catheter or by placement of a stent configured to continue to release the drug after the PTCA procedure. The delivery of the drug from coatings in these and other minimally invasive procedures can be complicated by the need both to have a coating that is durable during delivery, but which effectively delivers the drug when implanted in the region where local treatment is desired. Because natural biological environments are aqueous, it can occur that a coating containing a water-insoluble drug is sufficiently durable during travel to the intended delivery site, but then fails to optimally deliver the drug at the site. Needs thus exist for compositions, coatings, and coated implantable medical devices which enable the beneficial delivery of a drug locally to a site intended for treatment.

SUMMARY

One aspect of the present invention relates to a medical device including a base structure having a surface and a coating containing a drug and an excipient on the surface. In certain embodiments, the drug and excipient are present at a weight ratio of between 10:1 and 1:10 drug to excipient. In other embodiments, the excipient can be a terpeniod, for example a carotenoid, a phenolic compound including a polyphenol, a isoflavonoid, a curcuminoid, and a flavonoid which include flavones, flavonols, flavanones, and isoflavones. Specific examples include Chrysin, Tutin, Naringenin, and flavan-3-ols which can be gallate containing compounds like epigallocatechin gallate or compounds comprised of two or more flavan-3-ol units such as tannins, for example tannic acid.

In some embodiments, the coating includes a plurality of particles containing the drug encapsulated by the excipient. In other embodiments, the excipient is a gallate containing compound, epi gallo catechin gallate, epi catechin gallate or tannic acid. In yet other embodiments, the coating consists essentially of the excipient and the drug. For example, the coating can be free of a polymer or non-polymer carrier matrix.

In some embodiments, the drug is an immunosuppressive agent, an antiproliferative agent, a microtubule stabilizing agent, a restenosis-inhibiting agent or an inhibitor of the mammalian target of rapamycin. In other embodiments, the drug is a taxane compound, for example paclitaxel. The paclitaxel can be present in a crystalline form, for example dihydrate paclitaxel. The medical device can include an expandable device, for example a balloon or an expandable stent Another aspect of the present invention generally relates to a method for delivering a drug locally to tissue of a patient. In one embodiment, the method includes contacting a vessel wall of the patient with an embodiment of the medical device described herein. The device is maintained in contact with the vessel wall for a time sufficient to deliver the drug to the tissue of the patient.

Yet another aspect provides a method for treating a patient suffering from a disease or condition. In one embodiment, the method includes implanting a medical device as described herein in the patient and maintaining the implantable medical device within the patient for a time sufficient to deliver a therapeutically effective amount of the drug to a tissue of the patient. In various embodiments, the implantable medical device is a stent, a vascular stent, a ureteral stent, a catheter, a balloon, a balloon catheter, a stent graft, a wire guide or a cannula.

DETAILED DESCRIPTION OF THE PREFERRED EMBODIMENTS

Figure 1:
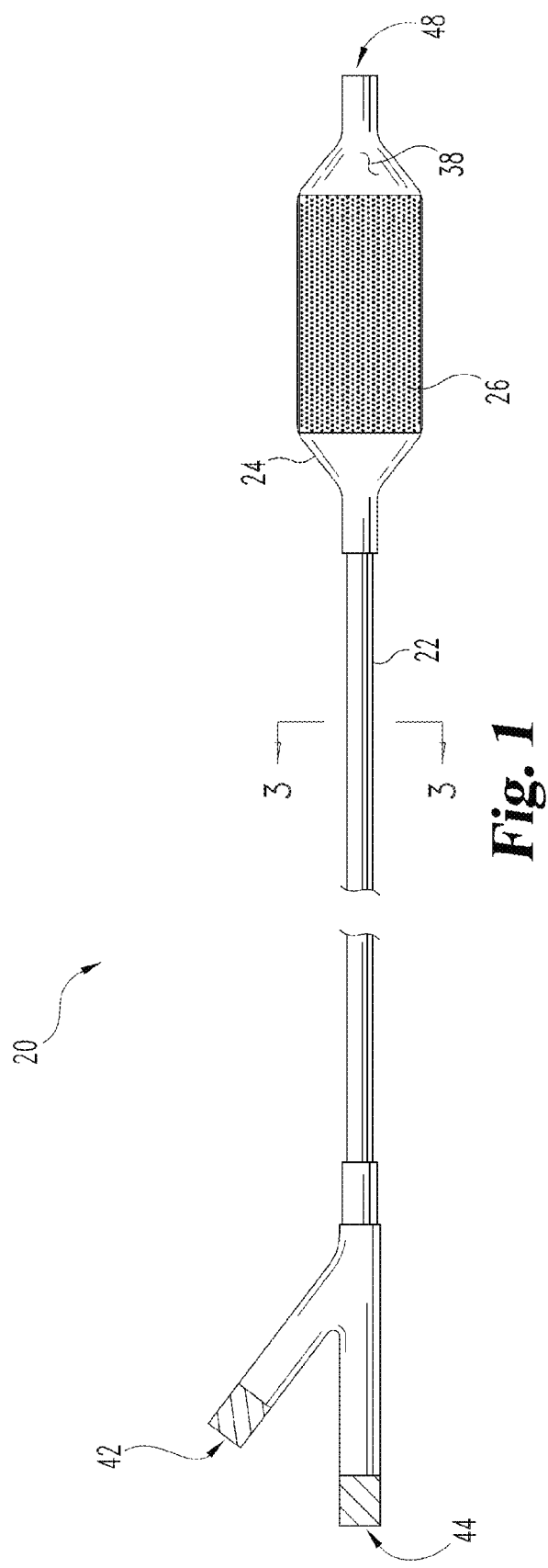
FIG. 1 provides a perspective view of a drug-delivering balloon catheter in accordance with one embodiment of the invention in an inflated condition.
Figure 2:
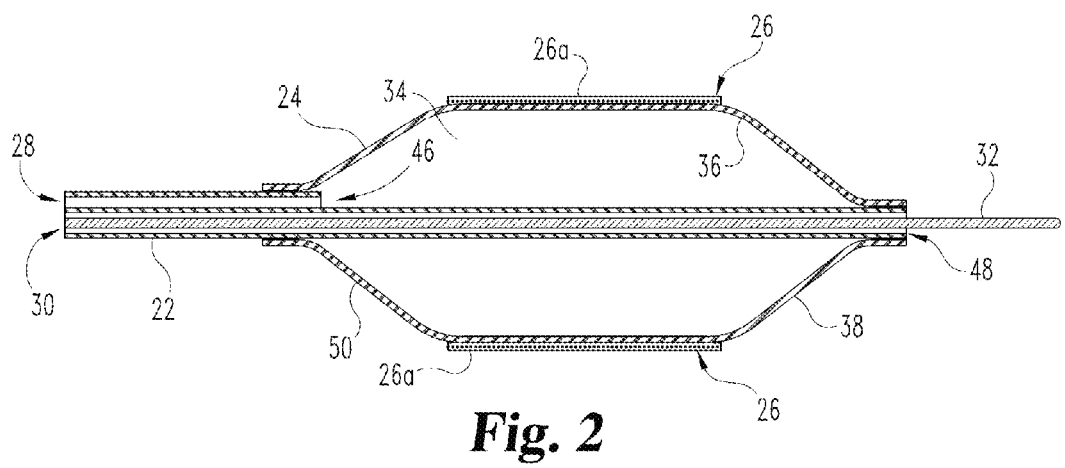
FIG. 2 provides a cross-sectional view of the balloon-mounted region of the balloon catheter of FIG. 1 taken along a central longitudinal axis.
Figure 3:
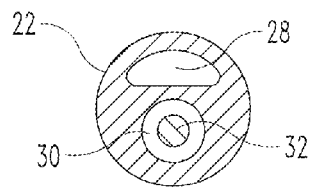
FIG. 3 provides a cross-sectional view of the catheter shaft of the balloon catheter of FIG. 1 taken along line 3-3 and viewed in the direction of the arrows.

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

In the discussions that follow, a number of potential features or selections of the drug, excipient, implantable medical device structure, or other aspects, are disclosed. It is to be understood that each such disclosed feature or features can be combined with the generalized features discussed herein, to form a disclosed embodiment of the present invention.

Definitions

The term "therapeutic effect" as used herein means an effect which induces, ameliorates or otherwise causes an improvement in the pathological symptoms, disease progression or physiological conditions associated with or resistance to succumbing to a disorder, for example restenosis, of a human or veterinary patient. The term "therapeutically effective amount" as used with respect to a drug means an amount of the drug which imparts a therapeutic effect to the human or veterinary patient.

The term "water-insoluble" as applied to a drug herein refers to a therapeutic agent having a solubility in water at 25° C. of less than 2 milligrams per milliliter (mg/ml). More preferably, the water-insoluble drug has a solubility in water at 25° C. of less than 1 mg/ml, even more preferably less than 0.1 mg/ml, and in certain embodiments less than 10 micrograms per milliliter (μg/ml).

Compositions

One aspect of the present disclosure relates to compositions including at least one drug and at least one excipient. In certain embodiments, the drug and the excipient are present at a weight ratio of between 10 to 1 and 1 to 10 drug to excipient. In other embodiments, the drug and excipient are present at a weight ratio of between 1 to 2 and 1 to 5 or between 1 to 1 and 1 to 5 drug to excipient. In yet other embodiments the drug and the excipient are present at a weight ratio such that the excipient encapsulates the drug to form microparticles of encapsulated drug.

The excipient can be a gallate containing compound such as, but not limited to, epi gallo catechin gallate (EGCG) or tannic acid. In other embodiments the excipient is a terpeniod, for example a carotenoid, a phenolic compound including polyphenols, isoflavonoids, curcuminoids, and flavonoids which include flavones, flavonols, flavanones, and isoflavones. Specific examples include Chrysin, Tutin, Naringenin, and flavan-3-ols which can be gallate containing compounds like epigallocatechin gallate or compounds comprised of two or more flavan-3-ol units such as tannins, for example tannic acid.

Yet other preferred compounds include compounds that contain the chemical moieties of gallate, catechin, tannin, catechol, or similar polyphenol moieties, including naturally derived compounds, as well as polymers that have been synthetically modified and covalently attached to these moieties.

Drugs within the scope of the present embodiments include antiproliferative agents immunosuppressive agents, restenosis-inhibiting agents, anti-cancer agents, analgesics/antipyretics, anesthetics, antiasthmatics, antibiotics, antidepressants, antidiabetics, antifungal agents, antihypertensive agents, anti-inflammatories, antineoplastics, antianxiety agents, sedatives/hypnotics, antianginal agents, nitrates, antipsychotic agents, antimanic agents, antiarrhythmics, antiarthritic agents, antigout agents, thrombolytic agents, hemorheologic agents, anticonvulsants, antihistamines, agents useful for calcium regulation, antibacterial agents, antiviral agents, antimicrobials, anti-infectives, bronchodilators, steroids and hormones.

Non-limiting examples of such drugs include doxorubicin, camptothecin, etoposide, mitoxantrone, cyclosporine, epothilones, napthoquinones, 5 fluorouracil, methotrexate, colchicines, vincristine, vinblastine, gemcitabine, statins (for example atorvastatin, fluvastatin, lovastatin, pitavastatin, pravastatin, rosuvastatin and simvastatin), steroids (for example cortisteroids, prednisilone and dexamethazone) mitomycin and derivatives or analogues of these agents.

Preferred drugs include water-insoluble drugs including water-insoluble antiproliferative agents, immunosuppressive agents and restenosis-inhibiting agents. In particular embodiments antiproliferative agents or immunosuppressive agents that are restenosis-inhibiting agents are utilized, which can be effective to inhibit restenosis of a vessel when applied to the inner wall of the vessel. In this regard, "restenosis-inhibiting" includes preventing or reducing the extent of restenosis. The inhibition of restenosis may be observed after a procedure in which the vessel wall is injured due to dilatation, for example during dilatation with a balloon of a balloon catheter and/or by expansion of a stent.

The water-insoluble restenosis-inhibiting agent may be a microtubule stabilizing agent such as paclitaxel, a paclitaxel analog, or a paclitaxel derivative or other taxane compound; a macrolide immunosuppressive agent such as sirolimus (rapamycin), pimecrolimus, tacrolimus, everolimus, zotarolimus, novolimus, myolimus, temsirolimus, deforolimus, or biolimus; an antiproliferative agent; a smooth muscle cell inhibitor; an inhibitor of the mammalian target of rapamycin (mTOR inhibitor); or a mixture of two, or two or more of any of these. These or other water-insoluble restenosis-inhibiting agents, including each agent or agent type identified herein, more preferably have a solubility in water at 25° C. of less than 1 mg/ml, even more preferably less than 0.1 mg/ml, and in certain embodiments less than 10 micrograms/ml. Paclitaxel, sirolimus, pimecrolimus, tacrolimus, everolimus, zotarolimus, novolimus, myolimus, temsirolimus, deforolimus, and biolimus are preferred water-insoluble restenosis-inhibiting agents for use herein (each known to have a water solubility of less than about 10 micrograms/ml).

In certain embodiments, the drug can be present in more than one polymorphic form. For example, the drug can be a taxane agent including one or more types of taxane agent(s). Taxane agent molecules having the same molecular structure may be arranged in different solid forms. Taxane agent molecules can exist in solvated or non-solvated solid forms that can be characterized and differentiated by one or more physical properties.

Typically, taxane agents in a solvated solid form dissolve more slowly in an aqueous environment, for example in blood, than non-solvated solid forms, but are less durable than the non-solvated solid forms. Once dissolved, the taxane agent molecules having identical molecular structures but originating from different solid forms are indistinguishable in solution.

In one embodiment, the taxane agent is paclitaxel. Solid forms of paclitaxel at room temperature include: amorphous paclitaxel ("aPTX"), dihydrate crystalline paclitaxel ("dPTX") and anhydrous crystalline paclitaxel. These different solid forms of paclitaxel can be characterized and identified using various solid-state analytical tools, for example as described by Jeong Hoon Lee et al., "Preparation and Characterization of Solvent Induced Dihydrate, Anhydrous and Amorphous Paclitaxel," Bull. Korean Chem. Soc. v. 22, no. 8, pp. 925-928 (2001), or in U.S. Pat. No. 8,642,063, issued Feb. 4, 2104, incorporated herein by reference. For example, amorphous and dihydrate taxane solid forms may be readily identified and differentiated by visual appearance and elution rates. The dihydrate taxane solid form typically has an opaque white color, while the amorphous dihydrate taxane solid form typically has a clear transparent appearance.

In one embodiment, the drug is paclitaxel, including a crystalline (dihydrate) form of paclitaxel. The paclitaxel can be encapsulated to form microparticles including dihydrate paclitaxel encapsulated by coating of excipient. In certain embodiments, the excipient is EGCG or tannic acid or a combination thereof.

The compositions of the present invention include those that may be administered by oral, parenteral (e.g., intramuscular, intraperitoneal, intravenous, ICV, transcatheter arterial chemoembolization, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

Coated Medical Devices

Other aspects of the present invention relate to medical devices incorporating a releasable component including a particulate coating including at least one drug encapsulated by an excipient. The excipient can be one of those compounds disclosed above for example, a gallate containing compound such as, but not limited to, EGCG or tannic acid. In certain embodiments, the medical devices are coated with or otherwise contain the excipients or compositions as disclosed above.

The medical device may be any of a wide variety of devices having an implantable medical device structure sized and shaped for temporary or permanent implantation in a human or veterinary patient. Medical devices having structures implantable in a bodily passage will often be used. The bodily passage may for example be a passage of the alimentary system, the urogenital system, the biliary system, or the cardiovascular system. Medical devices including a device structure implantable in the cardiovascular system are preferred, including for example those implantable in a vessel or chamber of the cardiovascular system of a human or animal patient through which blood travels. The passage may for example be a tubular passage such as an artery or vein, or may be a larger chamber such as a ventricle or atrium of the heart. Implantable medical devices that include structures that span or bridge between cardiovascular or other bodily passages are also contemplated. The implantable medical device can be adapted to be entirely or only partially implanted in a cardiovascular passage or other bodily passage.

The releasable component may be incorporated into the structure of the medical device and/or be present in a coating on one or more surfaces of the device. The releasable component may also be provided in the form of a fluid reagent for delivery by the device.

By way of example, the medical device can be or include a catheter, a wire guide, a stent, a coil, a needle, a graft, a filter, a balloon, a cutting balloon, a scoring balloon, a weeping (perfusion) balloon, or any combination of these. Suitable filters include for example vena cava filters such as the Cook CELECT® and Cook Günther TULIP® and Cook Gianturco-Roehm Bird's NEST® filters available from Cook Medical, Bloomington Ind., USA. Suitable stents include those without a covering, for example the Cook ZILVER® Cook ZILVER®-PTX stents available from Cook Medical. Suitable stents also include those with a sheath covering. Suitable coils include embolization coils. Suitable wire guides include for instance traditional wire guides as well as wire guides with an attached expandable structure for expansion within a blood vessel lumen, such as a coil, where the expandable structure can optionally carry the coating or coatings as disclosed herein. These or other implants, in certain preferred embodiments, have at least a portion that is configured to expand during deployment so as to contact walls of the passage in which they are implanted to anchor within the passage. In this regard, both self-expanding and force-expandable (e.g. balloon-expandable) stents or other implantable medical devices are contemplated as being within the scope of embodiments of the present invention.

The implantable medical device can be made from any suitable material or combination of materials. Illustratively, the implantable medical device can include a metal such as stainless steel, tantalum, titanium, nitinol, cobalt, chromium, nickel, molybdenum, manganese, gold, platinum, inconel, iridium, silver, tungsten, elgiloy, alloys of any of these, or another biocompatible metal; carbon or carbon fiber; a calcium-containing inorganic material such as a ceramic; a material composed of ceramic and metallic components (cermet); or a polymeric material. The material of construction for the implantable medical device structure can be biodegradable or non-biodegradable. Nonbiodegradable polymers that can be used include, for example, cellulose acetate, cellulose nitrate, silicone, polyethylene terephthalate, polyurethane, polyamide, polyester (e.g. Nylon), polyorthoester, polyanhydride, polyether sulfone, polycarbonate, polypropylene, high molecular weight polyethylene, and polytetrafluoroethylene, or mixtures of these. Biodegradable polymers that can be used include, for example, polylactic acid (PLA), polyglycolic acid (PGA), poly(lactic-co-glycolic acid) (PLGA), polyanhydride, polycaprolactone, polyhydroxybutyrate valerate, or mixtures of these. Biodegradable metals may also be used, including for example a biodegradable magnesium alloy.

In some preferred embodiments herein, the implantable medical device will be or include a balloon catheter, such as an angioplasty balloon catheter, a weeping or infusion balloon, a scoring balloon catheter or a cutting balloon catheter. Such a balloon catheter can include at least one balloon mounted on a catheter shaft, with the catheter shaft defining an inflation lumen fluidly communicating with an interior of the balloon. The catheter shaft can also define a guide member lumen, for receiving an elongate guidewire or other guiding member for the catheter. The guide member lumen can extend from a distal opening distal to the balloon to a proximal opening proximal to the balloon. The proximal guide member lumen opening can occur in a sidewall of the catheter shaft in a region proximate to the balloon (e.g. within about 10 cm proximal to the proximal end of the balloon) and which is positioned to reside within the patient during use of the balloon catheter, as occurs for example in "rapid-exchange" balloon catheter constructions, or can occur on the catheter shaft in a region positioned to reside external of the patient during use of the balloon catheter, as occurs for example in so-called "over-the-wire" balloon catheter constructions. The balloon catheter may include multiple balloons, usually in this case only two balloons, mounted in positions spaced longitudinally from one another on the catheter shaft. In such cases the balloons may share a common inflation lumen defined by the catheter shaft, or each may have a separate inflation lumen defined by the catheter shaft. In such balloon catheters having only two, or two or more balloons, the distal opening of the guide member lumen can occur distally of the distal-most balloon, and the proximal opening of the guide member lumen can occur proximal of the proximal-most balloon, in either rapid-exchange or over-the-wire type configurations as discussed above.

The balloon(s) of the balloon catheters herein may be configured for vascular angioplasty, and/or may have a balloon wall made of any suitable balloon wall material, typically a polymeric balloon wall material. The polymeric or other balloon wall material can be elastomeric, as in the case of an illustrative silicone elastomer, latex rubber elastomer, nylon elastomer, or polyurethane elastomer balloon film, where the balloon can expand upon inflation due to the expansion and thinning of the balloon wall material. The compliance of the balloon wall material in such elastomeric balloon applications is typically greater than 20% and more typically greater than 50%, and/or the burst pressure of such elastomeric balloons will typically be in the range of about 1.1 to about 2 atmospheres. In other embodiments, the polymeric or other balloon wall material can be inelastic, as in the case of a non-compliant or semi-compliant balloon (e.g. as commonly used in angioplasty and/or stent delivery balloons), where the balloon can expand upon inflation due to the unfolding of the balloon wall material from an initial folded configuration. Preferred balloon wall materials for non-compliant or semi-compliant balloons include polyamide (e.g. as in Nylon balloons), polyethylene terephthalate (PET), or polyurethane polymers. At least a portion of and potentially the entirety of such an elongate, generally cylindrical outer surface can carry the drug and excipient as discussed herein, either as the sole coating carried by the generally cylindrical outer surface or in combination with one or more additional coatings carried by the generally cylindrical outer surface.

In other preferred embodiments herein, the implantable medical device will be or include a stent. Such a stent may for example be a force-expandable stent, such as a balloon-expandable stent, or a self-expanding stent. The stent may be made from any one of numerous metals and alloys, including those identified hereinabove. The structure of the stent may be formed in a variety of ways to provide a suitable intraluminal support structure having an outer surface for contact with the vessel wall upon implantation and an inner surface that faces the lumen of the vessel and that can be generally opposite the outer surface. For example, the stent may be made from a woven wire structure, a laser-cut cannula, individual interconnected rings, or another pattern or design. In these or other constructions, the stent can include a plurality of struts each having an outer surface for contact with the vessel wall and an inner surface for facing the lumen of the vessel.

Such stents may be force-expandable, such as balloon-expandable, or self-expanding, as discussed above. Self-expanding stents of this type can be made of a resilient metal, preferably a superelastic metal alloy such as a superelastic nickel-titanium (Ni—Ti) alloy, as occurs for example in the ZILVER® nitinol stent commercially available from Cook Medical.

Any stent discussed above or elsewhere herein can have a stent surface carrying the releasable component as discussed herein, either as the sole coating carried by the stent surface, or in combination with one or more additional coatings positioned underneath and/or overtop the layer containing the releasable component. As well, surfaces of the stent not carrying the releasable component may optionally be bare (uncoated), or may carry one or more different coatings. Additionally, where the stent is mounted on a balloon of a balloon catheter for delivery, the surface of the balloon may carry the releasable component and potentially other layer(s) as described herein, and/or the surface of the stent may carry the releasable component and potentially other layer(s) as described herein. The practice of these and other variants will be within the purview of those of ordinary skill in the art in view of the teachings herein.

When the compositions are present in a coating on a surface of the device, the composition may constitute greater than 50, 75, 90, 95 or 99 percentage by weight of the coating. In certain embodiments, the coatings include less than about 5, 2, 1, 0.5, 0.1, 0.05 or 0.01 percentage by weight of materials other than the drug and the excipient. In other embodiments, the coatings include less than about 5, 2, 1, 0.5, 0.1, 0.05 or 0.01 percentage by weight of materials, such as polymers or other non-polymer carriers, that alter the release rate of the drug from the device when implanted.

Preferred drugs used in conjunction with implantable medical devices include water-insoluble antiproliferative agents, immunosuppressive agents, and restenosis-inhibiting agents. Particularly preferred are water-insoluble restenosis-inhibiting agents, such as those described above. In certain preferred embodiments, paclitaxel is the only drug included in combination with the device.

The drug can be incorporated in the device at any suitable level. Typically, when coated onto a device such as a stent or a balloon, the drug will be incorporated at a level of about 0.1 to about 1000 micrograms per $mm^2$, or about 0.1 to about 100 micrograms per $mm^2$, and in certain preferred forms about 0.1 to about 10 micrograms per $mm^2$ or about 0.5 to about 2 micrograms per $mm^2$ of the coated surface. Where two or more drugs are included in the coating, the above-recited levels can apply to the combined weight of all the drug(s), or to the drug(s) individually. It will also be understood that the coating may contain variations in the level of drug in different regions of the coating either due to manufacturing variances or intentional design criteria. Thus, the present invention contemplates coatings in which the level of drug(s) is substantially uniform over the entire area covered by the coating, or in which the level of drug(s) differs substantially in one area of the coating as compared to another area covered by another area of the coating. In certain preferred embodiments, paclitaxel is incorporated at a level in the range of 1 microgram per $mm^2$ to 10 micrograms per $mm^2$, or in the range of 2 micrograms per $mm^2$ to 6 micrograms per $mm^2$, or in the range of 0.5 micrograms per $mm^2$ to 2 micrograms per $mm^2$ either as the only drug in the coating or in combination with one or more additional drugs In particularly beneficial implantable medical devices of the invention, such paclitaxel-containing coatings are carried on a surface of a stent, including for example any stent described herein, and/or on a surface of a balloon of a balloon catheter, including for example any balloon catheter described herein.

The drug will typically be incorporated in the device in a therapeutically effective amount. In this regard, it will be understood that where the drug is a restenosis-inhibiting agent, the restonosis-inhibiting agent will be incorporated in the coating in an amount that is effective to inhibit restenosis when the implantable medical device (e.g. a balloon or stent) is deployed so as to deliver the drug from the implantable medical device to a wall of the artery, vein or other vessel or passage that is being treated by the device. As will be recognized, the level of a drug that will be therapeutically effective will vary in accordance with the particular drug in use, the implantable medical device in use, the implant site, the condition to be treated, the composition of the coating including the drug, and other potential factors. Through routine experimentation in view of the disclosures herein the achievement of a therapeutically effective amount of drug will be within the purview of those of ordinary skilled in the field.

The excipient can be included in the device in an amount effective to increase the rate of release of the drug from the device at a site of implant of the implantable medical device structure. This capacity can be demonstrated in, for example, in vivo testing, or in vitro testing where the level of the excipient are observed to increase the rate of release of the drug(s) in water, or in an aqueous medium such as blood serum or a 0.2 weight % aqueous solution of Heptakis (2,6-O-methyl)-beta-cyclodextrin (HCD), under static conditions at a temperature of 37° C.

In embodiments in which the releasable component is contained within or in a layer coating the implantable medical device, the excipient observed to increase the amount of drug released when implanted, by 10, 20, 30, 40, 50 75, 100, 125, 150, 200, 300 or 400 percentage as compared to a device that is identical except for the absence of the excipient.

In certain other embodiments, the excipient is observed to increase the delivery of the drug across a vessel wall and into the tissue of the patient. The increase in the amount of the drug delivered to the tissue of the patient from a device including the excipient may depend upon a number of factors, such as the nature of the vessel in which the composition is placed or device is implanted, as well as the environment within the vessel and the construction of the implantable device.

However, the increase in the amount drug delivered through a vessel wall may be characterized in an ex vivo assay in which the implantable device is placed in a section of the appropriate vessel and incubated in a buffer solution for a fixed time. In one such assay, a device, for example, is placed in a section of porcine ureter, which is hydrated in a Phosphate Buffered Saline buffer. The ureter is incubated in a closed container for a fixed time, for example 5 minutes at 37 deg. C. After the incubation period, the drug present in the ureter tissue is extracted using an extraction solution, such as an enzyme solution, organic solvent, organic/aqueous mixture, or acidified mixture. The extraction solution used is dependent on the drug being extracted. The amount of drug present in the ureter and in the device is determined using, for example, an appropriate HPLC method.

In certain embodiments, the claimed devices include excipient sufficient to increase the amount of drug delivered, as measured by this assay, by at least 5%, 10%, 15%, 20%, 25%, 30%, 40%, 50%, 70%, 100%, 150% or 200% compared to the amount of drug delivered, under the same conditions, from an otherwise identical device that does not include the excipient. In other embodiments, the devices include excipient sufficient to increase the amount of drug delivered, as measured by this assay, within a period of 1, 5, 15, 30, 60, 120, 300, 500 or 1000 minutes by at least 5%, 10%, 15%, 20%, 25%, 30%, 40%, 50%, 70%, 100%, 150% or 200%. In yet other embodiments, the claimed devices include an amount of excipient sufficient to increase the amount of drug delivered, as measured by this assay, within a period of 1, 5, 15, 30, 60 or 120 days by at least 5%, 10%, 15%, 20%, 25%, 30%, 40%, 50%, 70%, 100%, 150% or 200%.

In certain embodiments, the excipient is effective to deliver a therapeutically effective amount of the drug to patient tissue in a time period of about 5 minutes or less after implantation of the implantable medical device. More preferably, such time period is about 3 minutes or less, even more preferably about 2 minutes or less, and most preferably about 1 minute or less, e.g. in the range of about 20 seconds to about 1 minute. Such embodiments configured for relatively rapid delivery are especially beneficial when the releasable component is carried by a surface of a temporarily implantable medical device structure, for example a balloon of a balloon catheter, including any balloon catheter and in any coating arrangement described herein.

In other embodiments, the excipient increases the durability of the coating to resist the undesirable premature release of the drug from a device prior to delivery to a point of treatment within a body vessel. For example, the excipient can decrease the amount of drug released prematurely during folding and unfolding of a balloon portion of a balloon catheter or during crimping of an expandable stent. Likewise, the excipient may decrease the amount of drug loss during delivery of a medical device, such as a balloon or stent, to the treatment site.

In certain embodiments, coated stents disclosed herein exhibit a drug amount loss of less than about 10%, more preferably less than about 8%, 6%, 4%, 3%, 2%, 1% or 0.5% and most preferably less than about 0.1% upon crimping to a diameter of 6 French (6 F) and expansion. In other embodiments, coated balloons disclosed herein exhibit a drug amount loss of less than about 10%, more preferably less than about 8%, 6%, 4%, 3%, 2%, 1% or 0.5% and most preferably less than about 0.1% during folding and unfolding of the balloon.

In those embodiments in which the releasable component is contained as a coating layer, any of a wide variety of coating patterns may be used to constitute a material coat on the medical device. The coating layer can be directly adhered to a surface of an implantable structure of the medical device and provide an outermost surface over the implantable structure, and/or to constitute the entirety of the overall material coat on the implantable structure. In other embodiments, an overall material coat adhered to the implantable structure of the medical device can include one or more different coatings positioned underneath the layer including the releasable component (e.g. as in a polymeric or other primer coating, or a different drug coating, adhered directly to the surface of the medical device), one or more different coatings positioned overtop the layer including the releasable component (e.g. as in a polymeric or other protective or diffusion barrier coating), or both. As well, there may be one or more different coatings adjacent the layer including the releasable component, and/or multiple layers including the releasable component may be carried by the implantable medical device at locations discrete from one another. The layer including the releasable component may be present in an aperture(s) such as a well(s), groove(s) or hole(s) defined in the implantable medical device (e.g. in a stent) or may partially coat or completely coat the implantable medical device or a given surface (e.g. inner, outer or side surface) of the implantable medical device. These and other overall device coating arrangements can be utilized.

The layer including the releasable component can be carried by any suitable surface of the implantable medical device structure. The layer including the releasable component can be carried by, and in some embodiments only by, a surface or surfaces of the implantable medical device configured for contact with patient tissue when the device is implanted. For example, in some embodiments the layer including the releasable component is carried by a surface of a balloon of a balloon catheter, or by a surface of a stent, which is configured for contact with a wall of a vessel when the balloon is implanted (usually temporarily) or when the stent is implanted (usually permanently). In particular embodiments, in the case of a balloon of a balloon catheter which inflates to provide a substantially cylindrical outer surface as discussed above, the layer including the releasable component is carried by such substantially cylindrical outer surface, either partially or completely covering the substantially cylindrical surface. In the case of a stent having an outer surface as discussed above, the layer including the releasable component can be carried by the outer surface, either partially or completely covering the outer surface.

The layer including the releasable component and any other coating layers present can be incorporated as a part of the implantable medical device by any suitable method. This layer and any other coating layer can be formed on a surface of the implantable medical device. For example, the layer or other coating layer(s) can be formed by a method that includes dipping, spraying, showering, dripping, or otherwise applying a medium containing the coating ingredients, and optionally a substance such as a solvent can be removed from the medium to leave the coating adhered to the implantable medical device. Spray coating is one preferred form of applying the coating materials to the surface of the implantable medical device, and in particular embodiments ultrasonic spray coating will be utilized. During spray coating or other coating operations, the implantable medical device can be moved relative to a sprayer or other applicator of the coating ingredients. This can occur by moving the implantable medical device (including for example rotating the device or at least the portion to be coated), moving the sprayer or other applicator, or both. Multiple application passes or steps will typically be utilized to increase the thickness of the layer including the releasable component or other coating layer(s) and control the levels of the drug, excipient, or other ingredients applied to the implantable medical device. In spray or other application processes, areas of the implantable medical device adjacent to areas desired for coating can optionally be masked to prevent the application of coating materials to the masked areas, and/or portions of applied coating materials can be removed to selectively leave a layer including the releasable component or other coating in a desired region or regions of the device.

The layer including the releasable component can be constituted entirely of the drug and excipient, or may, for example, include a biostable polymer, where the polymer remains attached to the device structure as releasable component released. Alternatively, or in addition to the biostable polymer, this layer may include a bioabsorbable polymer. Such a polymer layer can include a polymeric matrix, e.g. made using a suitable polymer as identified herein, and in certain forms will be a porous layer that releasably contains an admixture including the drug and excipient in the pores thereof.

In certain embodiments, the releasable component is contained within the structure of the implantable device. For example, in those devices including a polymer component, the releasable component may be included in the mixture inserted in a mold to form at least part of the structure of the device. In certain embodiments, a mixture including the releasable component and a polymer is extruded to form at least part of the structure of the device. In other embodiments, the releasable component is imbibed into pores of a polymeric component of the device after this component is formed.

In certain aspects, a coated medical device as described herein, preferably comprising a stent and/or balloon catheter carrying the releasable component, can be configured to, and used to, treat any suitable body passage in a manner including release of the drug to the wall tissue of the body passage. The body passage may for example be a vein, artery, biliary duct, ureteral vessel, body passage or portion of the alimentary canal. A coated medical device as described herein may be used to treat a coronary artery, carotid artery, or a peripheral artery or vein, including as examples a renal artery or vein, iliac artery or vein, femoral artery or vein, popliteal artery or vein, subclavian artery or vein, intercranial artery or vein, aorta, vena cava, or others. In preferred embodiments, the coated medical devices will treat or prevent stenosis or restenosis in a body passage such as any of those identified herein, although treatment of other conditions is contemplated for other embodiments of the invention. In certain embodiments, the coated medical device is configured to, and used to, treat a narrowing of a peripheral artery or vein. Examples of such arteries include, but are not limited to, the femoral artery, the superficial femoral artery (artery below the branch for the profunda femoris artery), the popliteal artery and the infrapopliteal artery. Examples of such veins include, but are not limited to, the common iliac vein, external iliac vein, femoral vein, the popliteal vein and the lesser/greater saphenous vein.

With reference now to FIGS. 1-5, shown is one embodiment of a drug-delivering balloon catheter 20 in accordance with the embodiments of the invention. Balloon catheter 20 includes a catheter shaft 22 and a balloon 24 mounted thereon. A material coat 26 including a layer containing a drug and excipient 26a as described herein is carried by balloon 24. Catheter shaft 22 includes a first lumen 28 and second lumen 30. Lumen 28 is configured for inflation of balloon 24, and lumen 30 is configured to receive a guide wire 32 or other guide member to be used in conjunction with balloon catheter 20. Balloon 24 includes an interior region 34 designed to receive a liquid or other fluid for inflation of balloon 24. Balloon 24 has an inner wall 36 bounding balloon interior 34, and an outer wall surface 38. Layer 26 is adhered to outer wall surface 38 of balloon 24.

Balloon catheter 20 also includes a catheter hub 40 mounted to shaft 22. Catheter hub 40 defines a first opening 42 which fluidly communicates with balloon inflation lumen 28, and a second opening 44 which fluidly communicates with lumen 30 defined by shaft 22. Opening 42 of hub 40 and lumen 28 communicate with an opening 46 into the interior 34 of balloon 24, for passage of the inflation fluid for the balloon 24. Opening 44 of hub 40 and lumen 30 defined by a catheter shaft 22 extend to distal opening 48 of lumen 30, with distal opening 48 positioned distally of balloon 24.

Figure 4:
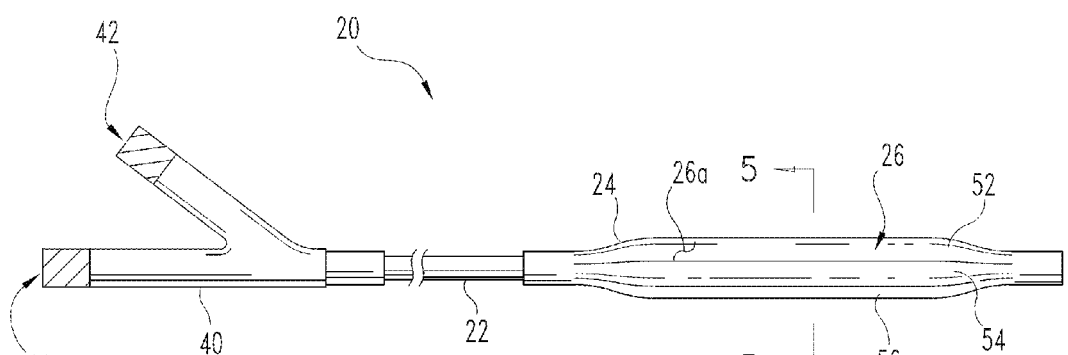
FIG. 4 provides a perspective view of the balloon catheter of FIG. 1 in a folded condition.
Figure 5:
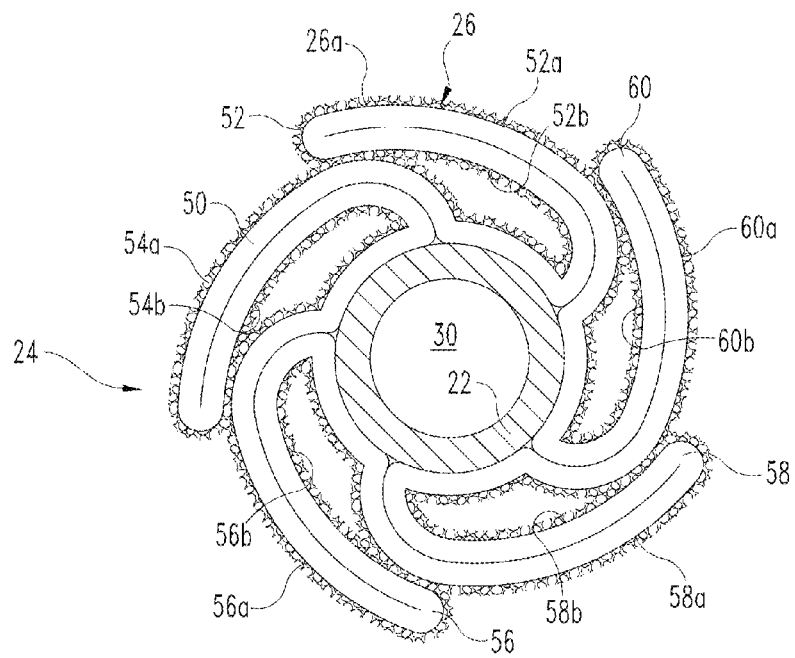
FIG. 5 provides a cross-sectional view of the balloon catheter of FIG. 4 taken along line 5-5 and viewed in the direction of the arrows.

With reference to FIG. 5 still in conjunction with features shown in FIGS. 1-4, balloon 24 includes a balloon wall 50, for example defined by a conventional balloon film, typically made from a polymeric material such as one of those discussed hereinabove. Balloon wall 50 as shown in FIGS. 4 and 5 is in a folded condition, useful during insertion of balloon 24 into a vessel such as an artery or vein. In its folded condition, balloon 24 includes pleats 52, 54, 56, 58, and 60. As shown, pleats 52-60 are arranged in a spiral pattern with each pleat in a curved condition extending circumferentially around the portion of catheter shaft 22 over which they occur, with the pleats overlapping and thereby contacting one another along at least a portion of their length. In this folded arrangement, pleats 52, 54, 56, 58, and 60 include externally-exposed pleat surfaces 52a, 54a, 56a, 58a, and 60a, and internal non-exposed pleat surfaces 52b, 54b, 56b, 58b, and 60b. Correspondingly, material coat 26, which in the illustrated embodiment includes coating layer 26a, has externally-exposed portions positioned on externally-exposed pleat surfaces 52a-60a, and internal non-exposed portions positioned on internal non-exposed pleat surfaces 52b-60b. Also in this arrangement, because pleats 52-60 overlap with one another, regions of material coat 26 and its drug and excipient 26a are in contact with other regions of material coat 26 and its drug and excipient 26a. In reference to FIG. 5, it should be understood that the features shown therein are intended to be illustrative, and that in practice balloon 24 is typically tightly pleated and wrapped around catheter shaft 22 and thus there will often be little or no open space on the interior of pleats 52-60.

Figure 6:
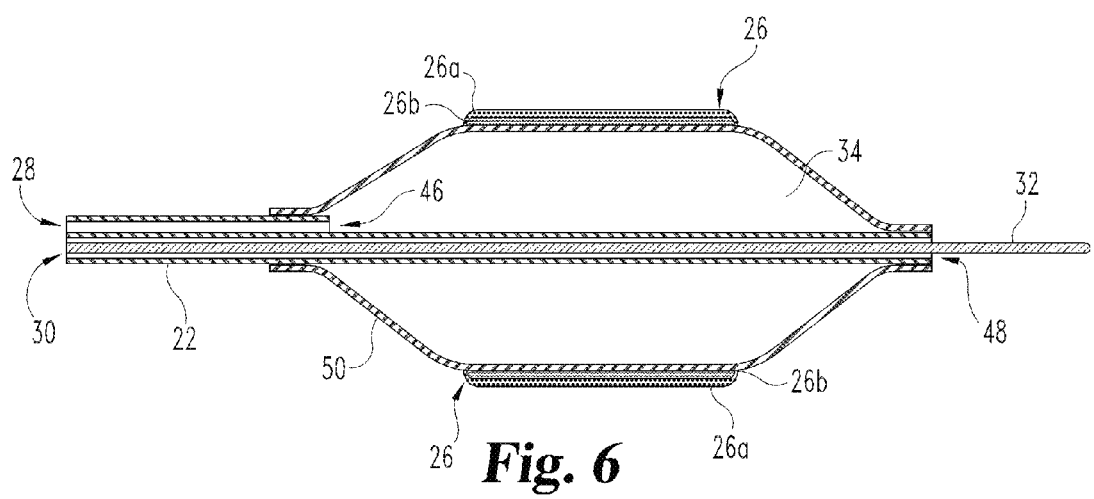
FIG. 6 provides a cross-sectional view of the balloon catheter of FIG. 1 taken along a longitudinal axis and illustrating an alternate coating configuration.

Referring now to FIG. 6, shown is another embodiment of a balloon catheter having features similar to those of balloon catheter 20 of FIGS. 1-5, but wherein material coat 26 includes a first coating layer 26a, which is a layer containing drug and excipient as described herein, and a second coating layer 26b different from this layer and positioned underneath coating layer 26a. Coating layer 26b may, in certain embodiments, be a polymeric primer layer as discussed above.

Figure 7:
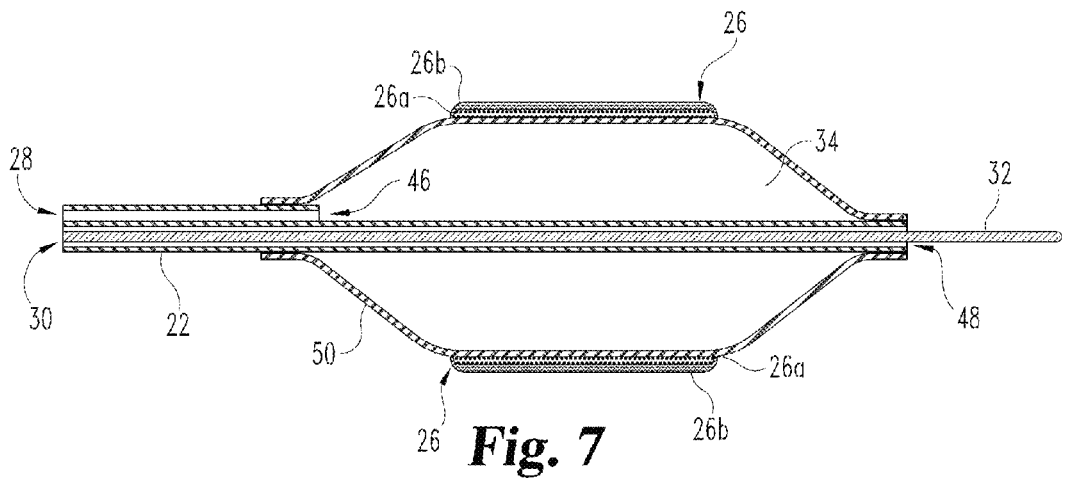
FIG. 7 provides a cross-sectional view of the balloon catheter of FIG. 1 taken along a longitudinal axis and illustrating another alternate coating configuration.

Referring to FIG. 7, shown is another embodiment of a balloon catheter similar to balloon catheter 20 of FIGS. 1-5, except wherein material coat 26 includes a first coating layer 26a, which is a layer containing drug and excipient as described herein, adhered directly to the outer surface 38 of balloon 24, and a second coating layer 26b positioned overtop coating layer 26a. Coating layer 26b of FIG. 7 may, in certain embodiments, be a polymeric protective layer and/or a polymeric diffusion barrier layer operable to control the release of the drug through the diffusion barrier layer.

Figure 5A:
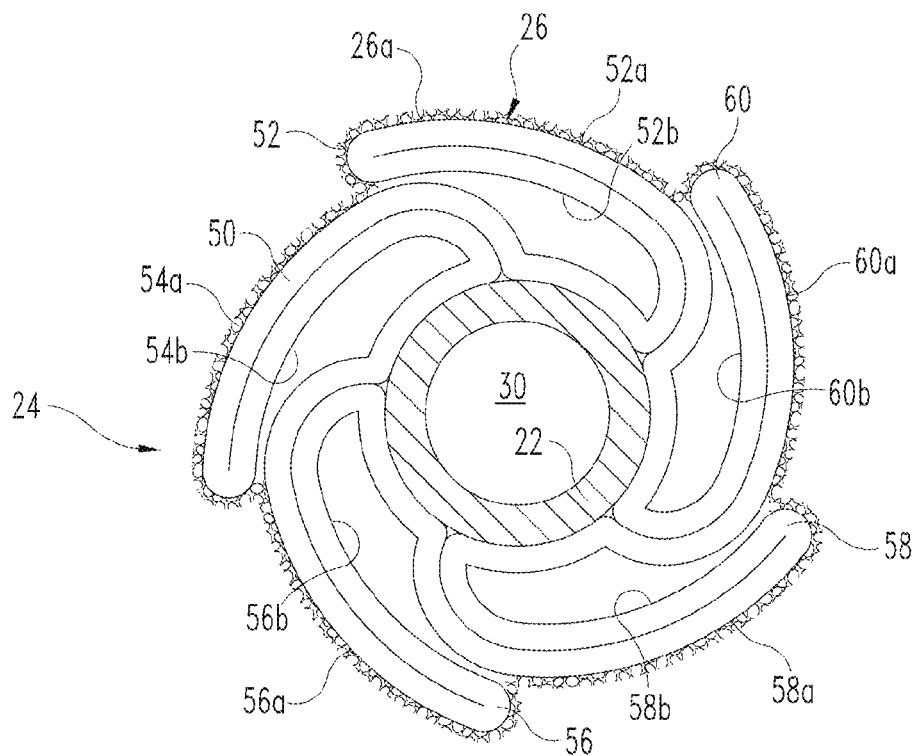
FIG. 5a provides a cross-sectional view illustrating an alternate coating pattern to that shown in FIG. 5.
Figure 5B:
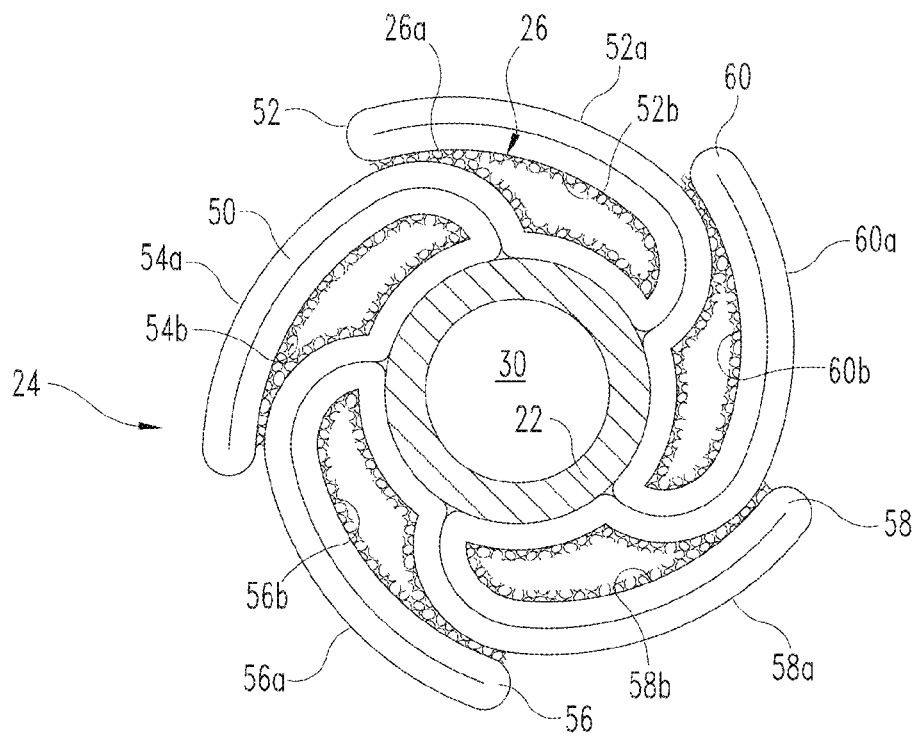
FIG. 5b provides a cross-sectional view illustrating another alternate coating pattern to that shown in FIG. 5.

FIGS. 5a and 5b show balloon catheter embodiments similar to that shown in FIGS. 1-5 except having a different coating pattern for material coat 26. In particular, in FIG. 5a, the material coat 26 including the layer containing drug and excipient 26a is carried only by the externally exposed surfaces 52a-60a of pleats 52-60. This configuration may be prepared, for example, by coating selected surface areas of the balloon 24 while in the inflated condition that will upon folding be positioned as externally exposed pleat surfaces 52a-60a, or by coating balloon 24 while in the folded condition under folding and coating conditions that coat only the externally exposed pleat surfaces 52a-60a. FIG. 5b discloses a balloon catheter embodiment in which the material coat 26 is carried only by internal non-exposed pleat surfaces 52b-60b. This configuration may be prepared, for example, by coating selected surface areas of the balloon 24 while in the inflated condition that will upon folding be positioned as internal non-exposed pleat surfaces 52b-60b, or by coating balloon 24 completely circumferentially while in the inflated condition, pleating and folding the balloon, and then removing the material coat 26 portions on the externally exposed pleat surfaces 52a-60a, for example mechanically and/or with a solvent or other medium capable of displacing the material coat 26. Layer 26a of the embodiments of FIGS. 5a and 5b can be applied in any suitable fashion, including using any of those methods described herein. As well, the material coat 26 of the embodiments of FIGS. 5a and 5b can, in other embodiments, be a multi-layer coating such as those shown and described herein, including those shown and described in conjunction with FIGS. 6 and 7.

Figure 8:
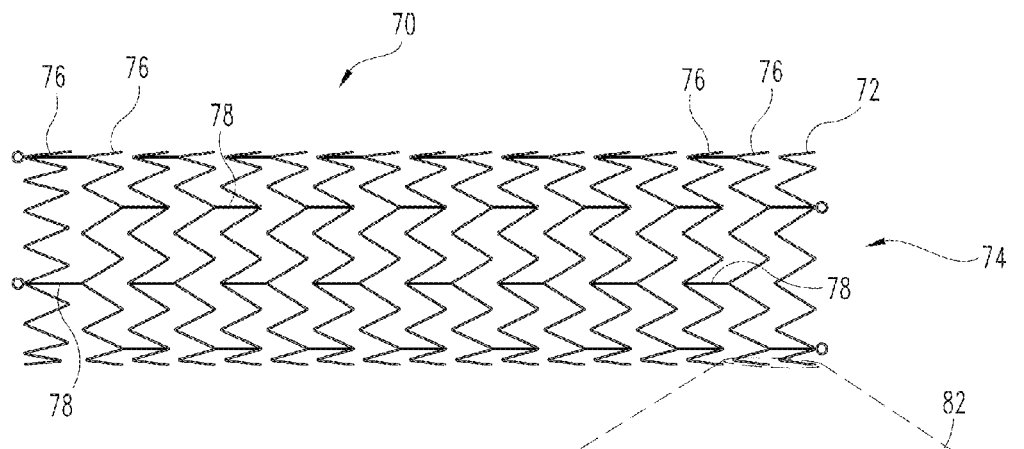
FIG. 8 provides a perspective view of a therapeutic agent-delivering stent in accordance with one embodiment of the invention.

FIG. 8 illustrates another embodiment of the invention. A stent 70 includes a stent body 72 defining a central lumen 74. Stent body 72 includes a plurality of longitudinally-adjacent segments 76 including struts defining a circumferential path about lumen 74 and a pattern of connecting strut segments 78 connecting adjacent segments 76. A coating 86 (see exploded section, lower right) including a layer containing drug and excipient 86a is carried by a surface of stent 70. In the illustrated embodiment, the layer 86a is adhered directly on the surface of stent 72 as the sole coating, although in other embodiments the stent coating 86 may be a multi-layer coating such as those shown and described herein, including those coatings shown and described in conjunction with FIGS. 6 and 7. Stent 72 has outer strut surfaces 80 configured for contact with a vessel wall such as an artery or vein wall of a patient. Stent 72 has an inner strut surface 82 opposite the outer surfaces 80 and generally facing the lumen 74. Stent 72 also has strut sidewall surfaces 84 between outer and inner strut surfaces 80 and 82. Strut outer surfaces 80 carry the material coat 86 over at least a portion of the outer surface of stent 72 and in certain embodiments over the entire or essentially the entire outer surface of stent 72. Stent 72 is desirably a self-expanding stent and is preferably made of a resilient metal, preferably a superelastic metal alloy such as a superelastic nickel-titanium (Ni—Ti) alloy, as occurs for example in the ZILVER® nitinol stent commercially available from Cook Medical, Bloomington, Ind., USA. Stent 72 can be manufactured using methods and materials disclosed herein for stents or otherwise, and the layer 86*a* and any other coating(s) present on the stent may have any composition taught herein and may be incorporated onto stent 72 in any suitable fashion, including any of those disclosed herein.

Figure 9:
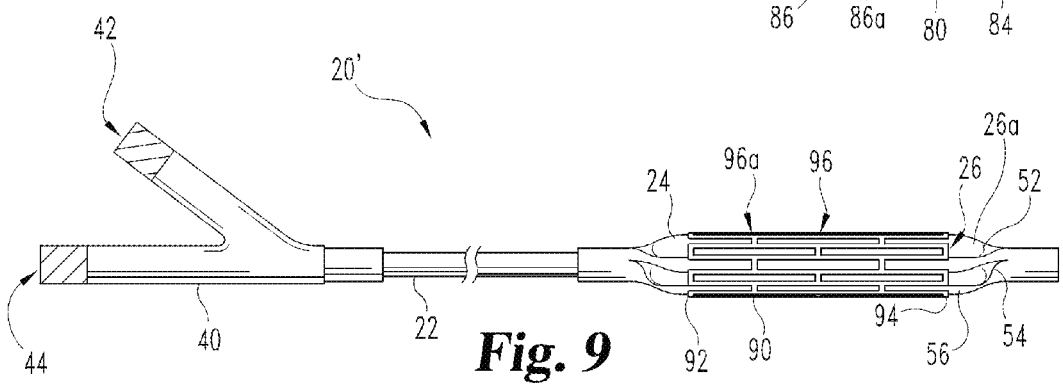
FIG. 9 provides a perspective view of a coated drug-delivering balloon catheter having a coated balloon-expandable stent mounted thereon in accordance with an embodiment of the invention.

FIG. 9 illustrates another embodiment of the invention. The implantable medical device 20' of FIG. 9 is similar to that shown in FIG. 4, except also having a balloon-expandable stent 90 mounted over balloon 24. Stent 90 has a proximal end 92 and a distal end 94. In this or other balloon catheters having a stent mounted on the balloon, either stent 90, balloon 24, or both, can carry a layer containing drug and excipient on a surface thereof. In the illustrated embodiment 20', the stent 90 has a material coat 96 including a layer containing drug and excipient 96*a* carried by an external surface thereof, and the balloon 24 has a material coat 26 including a layer containing drug and excipient 26*a* carried by the surface of balloon 24. The coating layer 26*a* can be carried on the balloon 24 so as to extend proximally of proximal end 92 of stent 90 and distally of distal end 94 of stent 90. In this fashion, the drug(s) of the layer containing drug and excipient, when balloon 24 is inflated in a vessel such as an artery or vein to dilate the vessel and implant the stent 90, can be applied to the vessel in regions extending proximally and distally of the stent 90. Where the drug(s) is or includes a restenosis-inhibiting agent, this can inhibit restenosis that may otherwise occur due to edge effects experienced at or near the proximal 92 and distal 94 ends of the stent 90.

The balloon and other components of the balloon catheter of device 20', and the stent 90, can be manufactured using methods and materials disclosed herein for the same or otherwise. The material coat 26 and/or material coat 96 can include a sole layer 26*a* or 96*a* adhered directly to the surface of balloon 24 or stent 90, respectively, although in other embodiments the balloon material coat 26 or stent material coat 96 may be a multi-layer coating such as those shown and described herein, including those coatings shown and described in conjunction with FIGS. 6 and 7. The layer containing drug and excipient and any other coating layer(s) present on the balloon and/or stent of device 20' may have any composition taught herein and may be incorporated onto the balloon 24 and/or stent 90 in any suitable fashion, including any of those disclosed herein.

Figure 10:
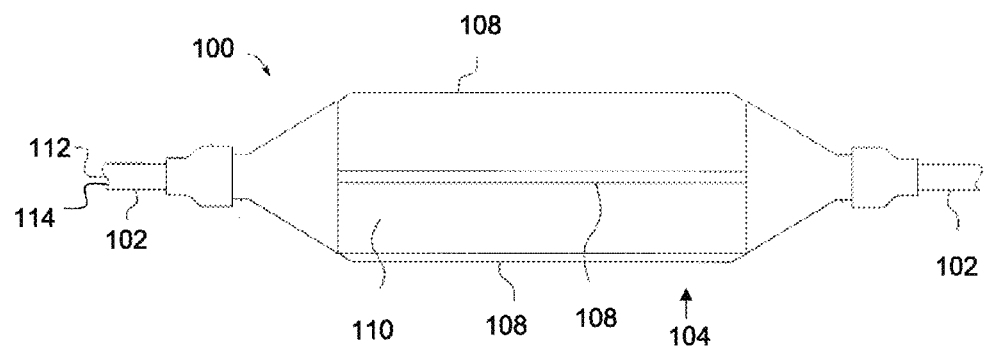
FIG. 10 provides a side view of a drug-delivering scoring balloon catheter in accordance with one embodiment of the invention in an inflated condition.
Figure 11:
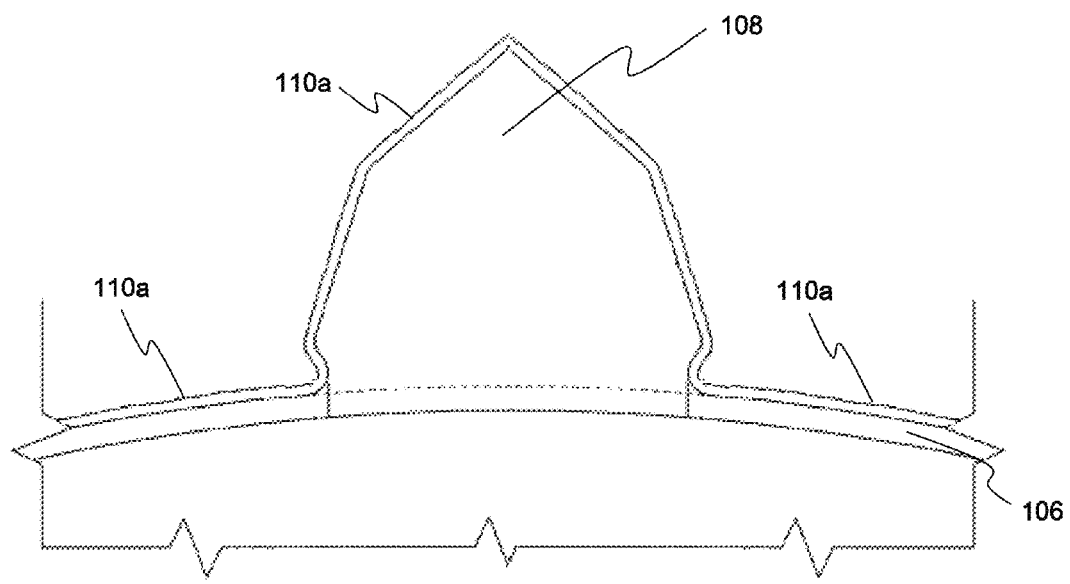
FIG. 11 provides an enlarged cross-sectional view of a dilation element of the scoring balloon catheter of FIG. 10 and adjacent balloon wall film portions.

FIGS. 10 and 11 depict another embodiment of the invention. FIG. 10 provides a side view of a drug-delivering scoring balloon according to one embodiment. FIG. 11 provides an enlarged cross-sectional view of a portion of the balloon of FIG. 10 including a dilatation element. More specifically, a drug-delivering scoring balloon catheter 100 includes a catheter shaft 102 and a balloon 104 mounted thereon. Balloon 104 has attached thereto, and preferably integrally formed with a balloon wall film 106 thereof, a plurality of dilation elements 108 projecting outwardly with respect to the balloon wall film 106 that spans between dilation elements 108. A material coat 110 including a layer containing drug and excipient 110*a* as described herein is carried by balloon 104 and in the specific illustrated embodiment by both the balloon wall film 106 and the dilation elements 108. Dilation elements 108 as depicted are trizoid-shaped elements; however, other shapes will be suitable for use in embodiments of the present invention, and dilation elements can be provided by separately attached or embedded articles or materials instead of being integrally formed with the balloon wall film. Catheter shaft 102 includes a first lumen 112 and second lumen 114. Lumen 112 is configured for inflation of balloon 104, and lumen 114 is configured to receive a guide wire or other guide member to be used in conjunction with balloon catheter 100. In the embodiment depicted, the layer containing drug and excipient 110*a* is directly adhered to outer wall surface of balloon 104 and in particular the outer surface of balloon wall film 106 and dilation elements 108. It will be understood that in other embodiments, this layer can be a part of a material coat that includes multiple layers, including any of those multiple layer coatings described hereinabove, and thus can have other coating layers underneath or overtop the layer containing drug and excipient. In addition or alternatively, the layer containing drug and excipient or material coat incorporating it can extend completely circumferentially around the balloon 104, coating both the dilation elements 108 and the balloon wall film 106 spanning between the dilation elements 108 (as in FIGS. 10 and 11), or selective portions of the balloon 104 can be coated. Illustratively, the dilation elements 108 can be completely or partially coated with the layer containing drug and excipient or other material coat including it while the balloon wall film 106 spanning between the dilation elements 108 can be uncoated or at least free of the layer containing drug and excipient or other material coat including it; or, the balloon wall film 106 spanning between the dilation elements 108 can be completely or partially coated with the layer containing drug and excipient or other material coat including it while the dilation elements 108 can be uncoated or at least free of the layer containing drug and excipient or other material coat including it. These and other coating arrangements will be suitable herein. As well, while the balloon 104 is shown in its expanded condition, it will be understood that embodiments herein will include balloon 104 in a folded condition, including for example any of those folded conditions, and structural features provided thereby, described hereinabove.

The following examples illustrate the present invention. The examples and embodiments described herein are for illustrative purposes only and modifications or changes in light thereof will be suggested to one skilled in the art without departing from the scope of the present invention.

Example 1: Coating of Paclitaxel and Additive onto the Surface of a Balloon Catheter Paclitaxel and tannic acid are coated onto a balloon catheter at a ratio of 1:2 paclitaxel to tannic acid. The final goal dose coated onto the balloon is approximately 1,300 micrograms per balloon, or about 1.5 micrograms/mm$^2$.

A working stock solution for balloon catheter coating is prepared. 66.6 mg of paclitaxel and 133.33 mg of tannic acid are weighed in a 22 mL glass vial. 10 mL of EtOH is transferred into the vial containing the drug and additive, which is then sonicated until the solution is homogenous. Typically, the mixture is sonicated for approximately 10 minutes.

A balloon (Cook Advance 18LP 7 mm×40 mm, Cook Medical Incorporated) is held horizontally within an apparatus capable of rotating the balloon along its longitudinal axis. The balloon is inflated so that it is completely expanded and the motor is turned on to begin rotation of the balloon. Using a 100 microL pipette, 65 microL of the above working solution is measured. Holding the pipette on the most proximal surface of the balloon the solution is slowly released from the pipette onto the balloon. During coating, the pipette tip is slowly dragged along the surface of the balloon while constantly releasing the solution. Care is taken to avoid gaps or overlaps of the coating. The first 65 microL is coated on the proximal ⅓rd of the balloon. The central and distal ⅓rd portions of the balloon were coated in the same manner.

The above steps are repeated twice to coat the remainder of the balloon catheter. A small volume drip of EtOH can be used after the initial drug coating to even out the coating and rinse the solution vial and pipette tip to ensure that all of the drug was coated onto the balloon. After the entire volume of solution is coated onto the surface, the ethanol is allowed to evaporate for up to 5 minutes, at which time the coating crystalizes and turns white. After the balloon has dried it is deflated, removed for the rotating apparatus, folded, and covered.

A similar balloon is inflated and coated using a spray coating method. Briefly, the stock solution is sprayed onto the surface of the inflated balloon using a stray gun and the solvent (for example, ethanol) allowed to evaporate. After the balloon has dried it is deflated, removed for the rotating apparatus, folded, and covered.

Example 2: Tissue Uptake Study

Flow loop testing is conducted to test the uptake of drug from a coated balloon into external porcine iliacs. The flow loop set up is as follows. The excess fat and tissue is removed from external porcine iliacs, which are cut to approximately 6 cm in length. The external iliacs are stored overnight in a refrigerator for testing the following day.

A flow loop testing circuit is set up as follows. Briefly, a porcine iliac is removed from the refrigerator and weighed. Black neoprene tubing is cut to the length needed to connect the inflow end of the porcine iliac to a reservoir containing approximately 150 mL of phosphate buffered saline (PBS) at 37 C. A three-way connector is present in the tubing to allow a balloon catheter to be inserted through the tubing and into the porcine iliac.

The outflow end of the porcine iliac is connected by neoprene tubing to form a return path to the reservoir. For example, the PBS can be contained in a 250 ml Buchner flask. This results in a completed loop for circulation of PBS. Any side branches of the porcine iliac are sealed off before it is immersed in a tissue bath containing approximately 1500 mL of 9% saline at 37 C.

A peristaltic pump is set to cycle the PBS at 480 ml/min and turned on to test that the PBS has a smooth flow and there is no leaking anywhere in the loop, especially in the tissue. To begin testing, a dilator and flexor sheath are inserted through the 3 way connector and to the site of inflation in the porcine iliac. The dilator is retracted. An inflation device is filed with approximately 20 mL of tap water and connected to the inflation lumen of a balloon coated using the procedure of Example 1. The balloon is degassed, fed into the sheath and tracked to the end in 40 seconds. This time is chosen to simulate the time typically taken for the balloon to reach the treatment site in vivo. After 40 seconds, the flexor is drawn back to expose the balloon to the tissue. After 20 seconds (60 seconds total), the balloon is inflated to 8 atm with the inflation device. The peristaltic pump is then turned off.

While maintaining 8 atm for 5 min, vials are prepared with 10 mL of EtOH for the balloon and tissue dosing. After 5 min at 8 atm, the balloon is removed from the flexor. The balloon is cut off the catheter into a vial with EtOH.

The peristaltic pump is turned on and the flow monitored for 1 min, allowing any particulate that isn't stuck in the tissue to wash away. After 1 min, the pump is turned off and the porcine iliac removed. The iliac is cut into 2 cm sections, which are placed into the prepared vials. 1 mL of the circulating PBS solution is pipetted into an HPLC vial. After the testing is completed, the vials are placed on a shaking incubator at 37° for 4 hours and then filtered through a 0.45 micron PVDF filter. All samples (balloon, PBS, and tissue) are run on the HPLC after the tissue extraction is finished.

Figure 12:
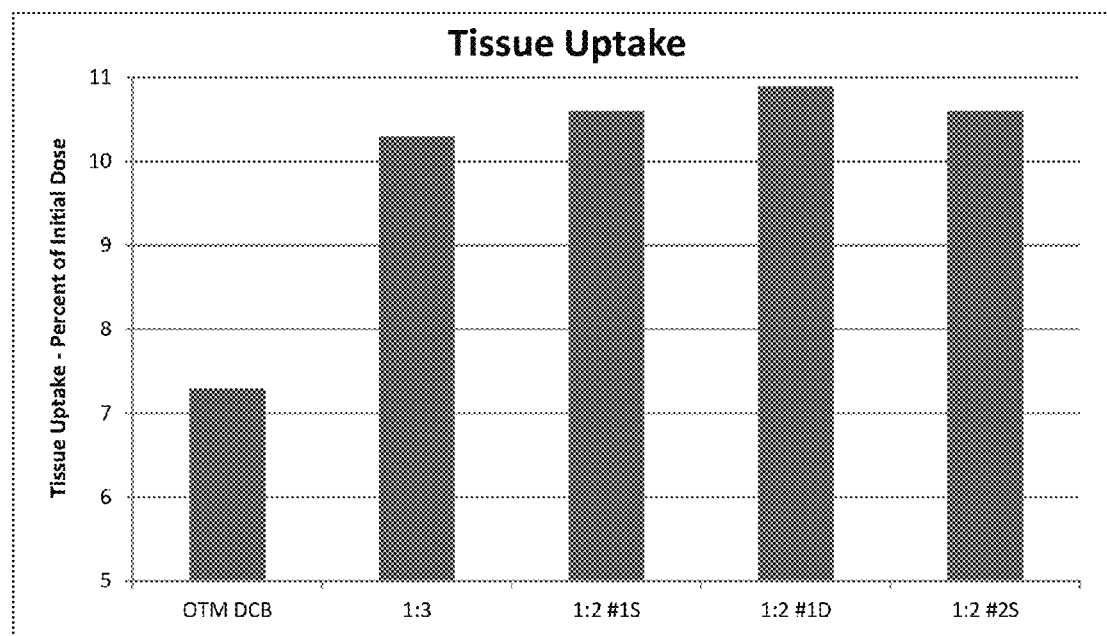
FIG. 12 is a graph showing flow loop results. The bars show the tissue uptake of drug as a percentage of the initial drug on the balloon.

FIG. 12 shows flow loop results obtained using the above protocol. Balloons are coated with a mixture of paclitaxel and tannic acid using a protocol similar to that described in Example 1. The ratio of paclitaxel to tannic acid is either 1:2 or 1:3. The coatings are performed using either a drip coating (1:2 #1D) or spray coating (1:3, 1:2#1S, 1:2#2S). The tissue uptake of drug is shown as a percentage of the initial drug on the balloon. The percentage uptake obtained using a commercially available drug coated balloon ("OTM DCB") is shown for comparison.

Example 3: Durability Testing Study

Durability testing is conducted to test the amount of drug loss from the balloon catheter during different phases of balloon delivery and deployment. Drug loss during folding, delivery to the site of inflation, and upon inflation is tested. To test for drug loss from folding, the balloon is coated and naturally deflated to recreate the folds, a vacuum is pulled, and a balloon cover is positioned over the balloon. Coating is performed using either a drip or spray coating method following the general protocol described in Example 1. After approximately 24 hours, the balloon cover is removed and the balloon is inflated. The balloon is then placed in a container and rinsed with 100% ethanol. The amount of drug remaining on the balloon is quantified on HPLC.

To test for drug loss during delivery of a balloon to the treatment site, the flow loop is set up as in Example 2 except that the pig vessel is replaced by a silicone tube. The PBS bath is not used in this experiment. The fluid flow is turned on and balloon is then tracked to the end of the silicone tube, without extending out of the tubing. This process is performed over a period equivalent to the tracking time of a balloon in vivo (about 40 seconds). After the appropriate period of time has passed the flow loop is shut off and the balloon is pushed out of the tubing and exposed to the air. At this time the end of the balloon catheter is cut off and the balloon is placed in a vial of 100% ethanol for drug quantification on HPLC.

To test for the drug loss during inflation of the balloon, the same set up as is used to test for drug loss during delivery it utilized. After approximately 40 seconds the balloon is inflated within the silicone tubing and the flow is shut off. The balloon is deflated after a very brief period of time, pushed out the end of the silicone tubing and the balloon is cut off and placed in a vial of 100% ethanol for drug quantification on HPLC.

Figure 13:
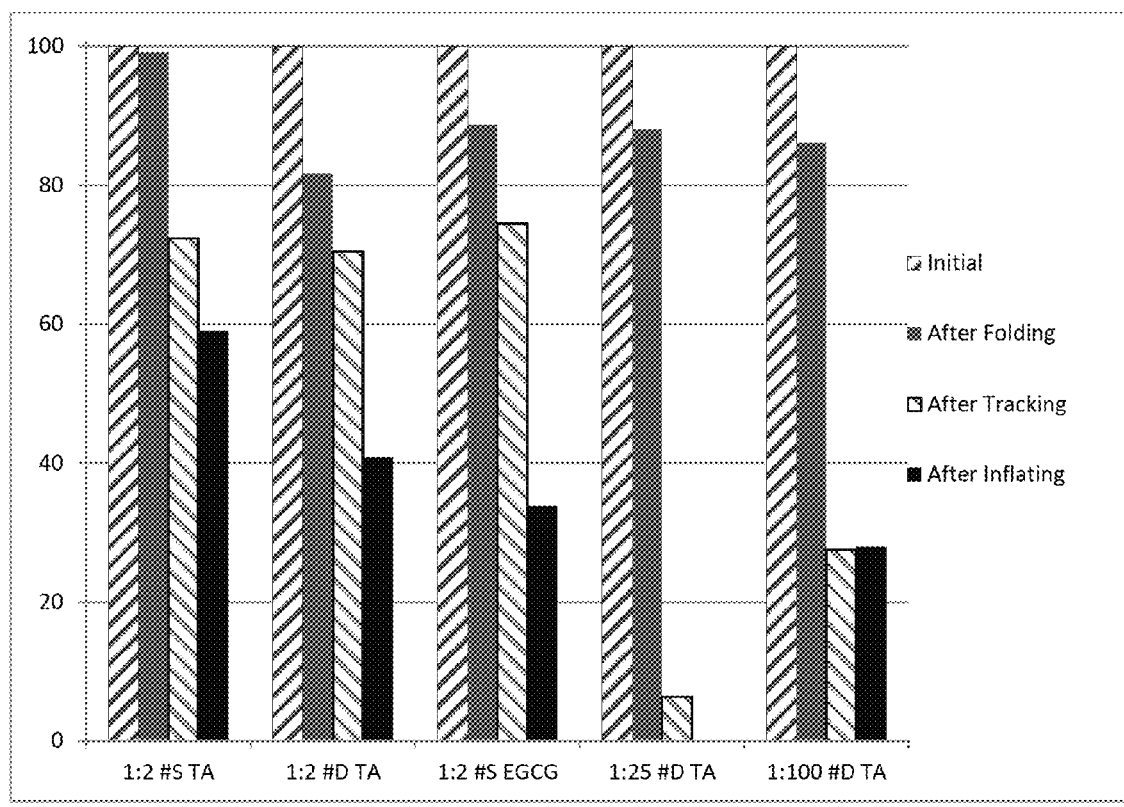
FIG. 13 is a graph showing the effect of tannic acid on the durability of a paclitaxel drug coating.

FIG. 13 shows the effect of tannic acid (TA) or EGCG on the durability of the drip (#D) or spray (#S) coating. The durability is better at a 1:2 (paclitaxel:tannic acid or EGCG) ratio, with less drug loss during balloon delivery and inflation in comparison to coatings at either 1:25 or 1:100 (paclitaxel:tannic acid.)

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

I claim:

1. A medical device comprising:
   a base structure having a surface, and
   a coating on the surface comprising a drug and an excipient, wherein the drug and excipient are present at a weight ratio of between 10 to 1 and 1 to 10 drug to excipient, and wherein the excipient is selected from the group consisting of, epi gallo catechin gallate, tannic acid and epi catechin gallate, and wherein the drug is a restenosis-inhibiting agent.

2. The medical device of claim 1, wherein the excipient is selected from a group consisting of epi gallo catechin gallate and tannic acid.

3. The medical device of claim 2, wherein the excipient is tannic acid.

4. The medical device of claim 2, wherein the excipient is epi gallo catechin gallate.

5. The medical device of claim 1, wherein the coating consists essentially of the excipient and the drug.

6. The medical device of claim 1, wherein the restenosis-inhibiting agent is selected from the group consisting of an immunosuppressive agent, an antiproliferative agent, a microtubule stabilizing agent, a smooth muscle cell inhibitor and an inhibitor of the mammalian target of rapamycin.

7. The medical device of claim 1, wherein the drug is selected from the group consisting of sirolimus, pimecrolimus, tacrolimus, everolimus, zotarolimus, novolimus, myolimus, temsirolimus, deforolimus and biolimus.

8. The medical device of claim 1, wherein the drug is paclitaxel.

9. The medical device of claim 8, wherein the paclitaxel is selected from the group consisting of amorphous paclitaxel, dihydrate paclitaxel, anhydrous crystalline paclitaxel and a mixture of at least two thereof.

10. The medical device of claim 8, wherein the paclitaxel is present in an amorphous and a crystalline form.

11. The medical device of claim 1, wherein the coating is free of a polymer or non-polymer carrier matrix.

12. The medical device of claim 1, wherein the coating comprises less than 1 percentage by weight of a polymer or non-polymer carrier matrix.

13. The medical device of claim 1, wherein the medical device is a balloon.

14. The medical device of claim 1, wherein the medical device is a stent.

15. The medical device of claim 1, wherein the medical device is selected from the group consisting of a stent, a vascular stent, a ureteral stent, a catheter, a balloon, a balloon catheter, a stent graft, a wire guide, and a cannula.

16. The medical device of claim 1, wherein the drug is present in more than one polymorphic form.

17. The medical device of claim 1, wherein the excipient is present in an amount effective to increase a rate of release of the drug from the medical device when implanted in a patient.

18. The medical device of claim 1, wherein the drug is a water-insoluble drug.

19. A medical device comprising:
   a balloon having an outside surface, and
   a coating on the outside surface, the coating comprising paclitaxel and an excipient, wherein the paclitaxel and excipient are present at a weight ratio of between 10 to 1 and 1 to 10 paclitaxel to excipient, wherein the paclitaxel is present in an amorphous and a crystalline form, and wherein the excipient is selected from the group consisting of a epi gallo catechin gallate and tannic acid.

* * * * *